United States Patent
Nasr et al.

(10) Patent No.: US 10,195,031 B2
(45) Date of Patent: Feb. 5, 2019

(54) IMPLANT

(71) Applicant: HIGHLIFE SAS, Paris (FR)

(72) Inventors: Malek Nasr, Paris (FR); Georg Börtlein, Paris (FR); Jean-Francois Ollivier, Paris (FR); Philippe D'Hiver, Paris (FR)

(73) Assignee: HIGHLIFE SAS, Paris (FR)

( * ) Notice: Subject to any disclaimer, the term of this patent is extended or adjusted under 35 U.S.C. 154(b) by 0 days.

(21) Appl. No.: 15/572,049

(22) PCT Filed: May 3, 2016

(86) PCT No.: PCT/EP2016/059895
§ 371 (c)(1),
(2) Date: Nov. 6, 2017

(87) PCT Pub. No.: WO2016/180677
PCT Pub. Date: Nov. 17, 2016

(65) Prior Publication Data
US 2018/0116799 A1 May 3, 2018

(30) Foreign Application Priority Data

May 8, 2015 (DE) .................. 10 2015 107 242

(51) Int. Cl.
*A61F 2/24* (2006.01)

(52) U.S. Cl.
CPC .......... *A61F 2/2457* (2013.01); *A61F 2/2412* (2013.01); *A61F 2/2442* (2013.01); *A61F 2/2463* (2013.01); *A61F 2/2403* (2013.01)

(58) Field of Classification Search
CPC .... A61F 2/2442; A61F 2/2445; A61F 2/2448; A61F 2/2451; A61F 2/2454; A61F 2/2457
See application file for complete search history.

(56) References Cited

U.S. PATENT DOCUMENTS

| 4,042,979 A | * | 8/1977 | Angell | A61F 2/2448 623/2.37 |
| 6,183,512 B1 | * | 2/2001 | Howanec, Jr. | A61F 2/2451 623/2.36 |

(Continued)

FOREIGN PATENT DOCUMENTS

WO 2004/112651 A2 12/2004

OTHER PUBLICATIONS

Aug. 9, 2016 International Search Report issued in International Patent Application No. PCT/EP2016/059895.

(Continued)

*Primary Examiner* — Alvin Stewart
(74) *Attorney, Agent, or Firm* — Oliff PLC

(57) ABSTRACT

An implant for implantation around a circumferential tissue structure in a heart, includes a flexible elongated component having a longitudinal axis and a first distal end portion, a second distal end portion and an intermediate portion extending between the first and second distal end portions, and an inner lumen extending longitudinally between the first and second distal end portions and through the intermediate portion; and a locking member for allowing the first distal end portion to be fixedly connected to the second distal end portion so as to provide the elongated component as a closed loop. The first distal end portion is provided with a first distal opening which connects the inner lumen with an outside of the component. The second distal end portion is provided with a second distal opening which connects the inner lumen with the outside of the component.

19 Claims, 12 Drawing Sheets

(56) References Cited

U.S. PATENT DOCUMENTS

| | | | |
|---|---|---|---|
| 6,250,308 B1* | 6/2001 | Cox | A61F 2/2448 128/898 |
| 6,503,274 B1* | 1/2003 | Howanec, Jr. | A61F 2/2451 623/2.37 |
| 7,347,870 B1* | 3/2008 | Andrieu | A61B 17/06166 623/2.36 |
| 7,722,668 B2* | 5/2010 | Moaddeb | A61F 2/2445 623/2.36 |
| 8,231,671 B2* | 7/2012 | Kim | A61F 2/2451 606/144 |
| 8,287,591 B2* | 10/2012 | Keidar | A61F 2/2445 623/2.36 |
| 8,632,588 B2* | 1/2014 | Kim | A61F 2/2451 623/2.36 |
| 9,622,864 B2* | 4/2017 | Annest | A61F 2/2466 |
| 9,770,332 B2* | 9/2017 | Bortlein | A61F 2/2466 |
| 9,907,547 B2* | 3/2018 | Gilmore | A61B 17/0401 |
| 2003/0229395 A1* | 12/2003 | Cox | A61F 2/2448 623/2.36 |
| 2006/0025858 A1* | 2/2006 | Alameddine | A61F 2/2445 623/2.37 |
| 2007/0100439 A1* | 5/2007 | Cangialosi | A61F 2/2442 623/2.11 |
| 2007/0135913 A1* | 6/2007 | Moaddeb | A61F 2/2445 623/2.37 |
| 2007/0233239 A1* | 10/2007 | Navia | A61F 2/2445 623/2.37 |
| 2007/0244555 A1* | 10/2007 | Rafiee | A61F 2/2445 623/2.11 |
| 2007/0276478 A1* | 11/2007 | Marmureanu | A61F 2/2445 623/2.11 |
| 2008/0262609 A1* | 10/2008 | Gross | A61B 17/064 623/2.36 |
| 2009/0248148 A1* | 10/2009 | Shaolian | A61F 2/2448 623/2.37 |
| 2012/0123531 A1* | 5/2012 | Tsukashima | A61F 2/2448 623/2.37 |
| 2012/0179246 A1* | 7/2012 | Kim | A61F 2/2451 623/2.36 |
| 2014/0276979 A1* | 9/2014 | Sauer | A61B 17/0469 606/144 |
| 2015/0100117 A1* | 4/2015 | Bortlein | A61B 17/00234 623/2.11 |
| 2015/0134057 A1* | 5/2015 | Rourke | A61B 17/0401 623/2.36 |
| 2015/0238314 A1* | 8/2015 | Bortlein | A61F 2/2427 623/2.11 |
| 2015/0245910 A1* | 9/2015 | Righini | A61F 2/2466 623/2.11 |
| 2015/0359632 A1* | 12/2015 | Navia | A61F 2/2454 623/2.36 |
| 2016/0262741 A1* | 9/2016 | Gilmore | A61B 17/0401 |
| 2017/0119489 A1* | 5/2017 | Kim | A61B 17/00234 |
| 2017/0156864 A1* | 6/2017 | Chang | A61F 2/2487 |

OTHER PUBLICATIONS

Feb. 3, 2016 German Office Action issued in German Patent Application No. 10 2015 107 242.4.

Aug. 9, 2016 Written Opinion issued in International Patent Application No. PCT/EP2016/059895.

* cited by examiner

IMPLANT

FIELD

The invention relates to implants, in particular to implants for surrounding a circumferential structure in a heart.

BACKGROUND

Globally heart valve diseases affect approximately 300000 people per year. These diseases involve abnormal tissue (e.g. excess tissue growth, tissue degradation, tissue hardening) or abnormal tissue position during the cardiac cycle (i.e. annular dilation, ventricular reshaping) and result in a degrading valve function such as blood leakage (valve insufficiency) or an increased resistance to blood flow in the natural flow direction (valve stenosis). Treatment of these diseases is possible by implanting an implant around a circumferential tissue structure in a heart or in the vicinity thereof.

Accordingly, an implant and related procedures are desirable.

SUMMARY

The invention provides an implant for implantation around a circumferential tissue structure in a heart, comprising a flexible elongated component which has a longitudinal axis and which has a first distal end portion, a second distal end portion and an intermediate portion extending between the first and second distal end portions, and an inner lumen, e.g. one (single) lumen, extending longitudinally between the first and second distal end portions and through the intermediate portion; and a locking means for allowing the first distal end portion to be fixedly connected to the second distal end portion so as to provide the elongated component as a closed loop; wherein the first distal end portion is provided with a first distal opening which connects the inner lumen with an outside of the component; wherein the second distal end portion is provided with a second distal opening which connects the inner lumen with the outside of the component; and wherein the intermediate portion is provided with a proximal opening which connects the inner lumen with the outside of the component, wherein the proximal opening is longitudinally spaced from both the first and second distal openings. The flexible elongated component consist, e.g., of one (single) part. That is, the flexible elongated component consist, e.g., of a one-piece hollow body forming the one (single) inner lumen longitudinally extending therethrough.

The said closed loop, which is formed after having fixedly connected the first distal end portion to the second distal end port, e.g., may be formed in a smooth ring (shape) (that is, e.g., in a ring shape which at least substantially excludes radial undulation and/or radial protrusions), which ring (shape) may be and/or may extend in one (single) plane.

Furthermore, the flexible elongated component may, e.g., be provided such that circumferential length of the said closed loop cannot be adjusted in the intermediate portion, but, e.g., may be provided such that the circumferential length may only be adjustable at the first and second distal ends, e.g. by means of the connection of the first and second distal ends of the flexible elongated component.

According to embodiments, one or both of the first and second distal openings may be a distal end opening provided in a distal frontal end of the corresponding first or second distal end portions.

According to embodiments, a longitudinal distance between the proximal opening and the first distal opening may at least substantially equal to a longitudinal distance between the proximal opening and the second distal opening.

According to embodiments, the proximal opening may have first and second proximal sub-openings, both of which may connect the inner lumen with the outside of the component and both of which may located adjacent to each other. For example, the longitudinal distance between the first and second proximal sub-openings may be smaller, e.g. at least ten or twenty times smaller, than the longitudinal distance between first distal opening and the first proximal sub-opening and/or the longitudinal distance between the second distal opening and the second proximal sub-opening.

According to embodiments, the longitudinal distance between the first distal opening and the first proximal sub-opening may be at least substantially equal to the longitudinal distance between the second distal opening and the second proximal sub-opening. According to embodiments, the first distal end portion can engage into the second distal opening. The locking means may comprise a protrusion which radially protrudes from an outside of the first distal end portion. When the first distal end portion is in engagement in the second distal opening, the anchor may radially engage with an inner portion of the second distal end portion so as to fixedly secure the engagement of the first distal end portion in the second distal opening.

According to embodiments, the protrusion may be formed as an anchor or barb.

According to embodiments, at least the inner portion of the second distal end portion may be provided in a flexible manner so as to allow the protrusion to radially expand the inner portion and to be longitudinally anchored in the inner portion of the second distal end portion.

According to embodiments, the implant may further comprise a restricting arrangement, by which a longitudinal movement of the first distal end portion into the second distal opening may be restricted.

According to embodiments, the restricting arrangement may comprise an outer sleeve provided on the second distal end portion. The outer sleeve may have a radial strength stronger than the radial strength of the distal end portion.

According to embodiments, an outer surface of the component may be treated with a tissue ingrowth promoting material and/or surface structure.

The invention further provides a system for implanting an implant around a circumferential tissue structure in a heart of a patient, comprising a flexible elongate continuous guide wire for surrounding the tissue structure, which has a first leg portion with a first free end portion, a second leg portion with a second free end portion, and a loop portion extending between and connecting the first and second leg portions, wherein the loop portion is for distally extending around the tissue structure and the first and second leg portions are for proximally extending from the tissue structure towards an outside of the patient so that their first and second free end portions, are accessible for a surgeon, and an implant as described herein, wherein the guide wire is disposable or is disposed in the inner lumen of the component in a manner so that the loop portion extends between the first and second distal end portions, the first leg portion extends from the loop portion through the first distal opening and through the proximal opening so that the first free portion is proximally exposed from the component, and the second leg portion extends from the loop portion through the second distal opening and through the proximal opening so that the second free end portion is proximally exposed from the component, and wherein the implant is moveable along the guide wire in a distal direction, with the first and second distal end portions being simultaneously moveable in a distally leading manner on the first and second leg portions onto the loop portion.

According to embodiments, the guide wire may be disposable or may be disposed in the inner lumen of the component in a manner so that the loop portion extends between the first and second distal end portions, the first leg portion extends from the loop portion through the first distal opening and through the first proximal sub-opening so that the first free portion is proximally exposed from the component, and the second leg portion extends from the loop portion through the second distal opening and through the second proximal sub-opening so that the second free portion is proximally exposed from the component.

According to embodiments, the system may further comprise first and second tubes. At least a portion of the first and second tubes may be removably located in the inner lumen of the component. The first and second tubes may removably extend at least through a (e.g. longitudinal) portion of the inner lumen of the component. In this respect, the first tube may extend through the proximal opening and/or the first proximal sub-opening of the component while a distal end opening of the first tube may be located in the inner lumen of the component longitudinally between the first distal opening and the proximal opening and/or the first proximal sub-opening. The distal end opening of the first tube may for example be located at a longitudinal level of the first distal opening of the component (e.g. without being exposed therefrom). Optionally, the first tube may also extend through the first distal opening of the component (that is, said distal end opening of the first tube may be located distally from the first distal opening of the component). The second tube may extend through the proximal opening and/or the second proximal sub-opening of the component while a distal end opening of the second tube may be located in the inner lumen of the component longitudinally between the second distal opening and the proximal opening and/or the second proximal sub-opening. The distal end opening of the second tube may for example be located at a longitudinal level of the second distal opening of the component (e.g. without being exposed therefrom). Optionally, the second tube may also extend through the second distal opening of the component (that is, said distal end opening of the second tube may be located distally from the second distal opening of the component). Proximal end openings of the first and second tubes may be located proximally from the proximal opening (e.g. the sub-openings thereof) of the component, e.g. proximally from a pusher head of a pusher catheter. The first leg portion of the guide wire may extend through the first tube and the second leg portion may extend through the second tube.

According to embodiments, the system may further comprise an outer catheter having proximal and distal outer catheter end portions with respective proximal and distal outer catheter openings and an outer catheter lumen. The guide wire, with the implant disposed thereon, may be disposable through the outer catheter lumen.

According to embodiments, the system may further comprise a pusher catheter having distal and proximal pusher catheter end portions with respective distal and proximal pusher catheter openings and a pusher catheter lumen. The pusher catheter may be configured so as to be disposable through the outer catheter lumen. The guide wire may be configured so as to be partly disposable through the pusher catheter lumen. The pusher catheter and the implant may be configured such that the implant, disposed on the guide wire which itself may be partially disposed in the pusher catheter lumen, can be distally pushed on and along the guide wire through the outer catheter lumen.

According to embodiments, the pusher catheter may be provided with a pusher head provided on the distal pusher catheter opening, the pusher head having a through opening sized so as to allow the first and second leg portions of the guide wire to pass therethrough and to prevent the component to pass therethrough. When the system comprises first and second tubes, the through opening may be sized such that the first and/or the second tube (e.g. with the guide wire passing therethrough) may pass through the through opening while the component is prevented from passing therethrough.

According to embodiments, the through opening may comprise first and second sub-through openings which are sized so as to allow the first and second leg portions, respectively, of the guide wire to pass therethrough. When the system comprises a first tube, the first sub-through opening may be sized such that the first tube (e.g. with the guide wire passing therethrough) may pass through the first sub-through opening, while the component is prevented from passing therethrough. When the system comprises a second tube, the second sub-through opening may be sized such that the second tube (e.g. with the guide wire passing therethrough) may pass through the second sub-through opening, while the component is prevented from passing therethrough.

According to embodiments, the pusher head may be rotatable relative to the pusher catheter about a longitudinal axis of the pusher catheter.

The invention also provides a method for disposing and forwarding an implant on a guide wire of a system as described herein, comprising threading the first leg portion of the guide wire with its first free end portion into the first distal opening and out through the proximal opening and/or the first proximal sub-opening, threading the second leg portion of the guide wire with its second free end portion into the second distal opening and out through the proximal opening and/or the second proximal sub-opening, and pushing the component on and along the guide wire towards the loop portion thereof to distally approach the first and second distal end portions from opposite direction so as to meet and connect to each other in the loop portion of the guide wire. Such a method may for example be employed during an implantation procedure as a method for disposing and forwarding an implant on a guide wire of a system to a patient. However, such a method may also be practiced without any involvement of a patient, e.g. for training purposes. In such a case, the method may not involve/comprise any treatment of the human or animal body by surgery or therapy.

This document also describes a procedure for providing an implant around a circumferential tissue structure in a heart of a patient using the system as described herein, comprising the steps: a) forwarding the first free end portion of the guide wire from an outside of the patient to the tissue structure, around the tissue structure and back towards the outside of the patient, so that the loop portion of the guide wire extends distally around the tissue structure and the first leg portion extends proximally from the tissue structure towards the outside of the patient and the second leg portion extends proximally from the tissue structure towards the outside of the patient, so that the first and second free end portions of the first and second, respectively, leg portions are accessible for a surgeon, b) threading the first leg portion of the guide wire with its first free end portion into the first distal opening and out through the proximal opening and/or the first proximal sub-opening of the component, threading the second leg portion of the guide wire with its second free end portion into the second distal opening and out through the proximal opening and/or the second proximal sub-opening of the component, c) pushing the implant on and along the guide wire towards the loop portion thereof to distally approach the first and second distal end portions of the component simultaneously from opposite directions so as to meet and connect to each other in the loop portion of the guide wire, and d) fixedly connecting the first and second distal end portions of the component.

According to embodiments, the procedure may further comprise forwarding the distal outer catheter end portion from the outside of the patient so as to be located adjacent to the tissue structure, and carrying out steps a) to c) through the outer catheter lumen.

According to embodiments, the procedure may further comprise, after step b): threading the first and second leg portions with their respective first and second free end portion through the distal pusher catheter opening, into the pusher catheter lumen and through the proximal pusher catheter opening to the outside of the pusher catheter, inserting the implant and the distal pusher catheter end portion threaded on the guide wire through the proximal outer catheter opening into the outer catheter lumen, wherein step c) comprises pushing the implant on and along the guide wire towards the loop portion thereof through the outer catheter lumen by distally moving the pusher catheter through the outer catheter lumen to distally approach the first and second distal end portions of the component simultaneously from opposite direction so as to meet and connect to each other in the loop portion of the guide wire.

According to embodiments, threading the first leg portion of the guide wire with its first free end portion into the first distal opening and out through the proximal opening and/or the first proximal sub-opening of the component of step b) may comprise: threading the first leg portion of the guide wire with its first free end portion proximally into the first tube and proximally therethrough, so as to dispose the first leg portion of the guide wire through the first tube, and wherein threading the second leg portion of the guide wire with its second free end portion into the second distal opening and out through the proximal opening and/or the second proximal sub-opening of the component of step b) may comprise threading the second leg portion of the guide wire with its second free end portion proximally into the second tube and proximally therethrough so as to dispose the second leg portion of the guide wire through the second tube.

According to embodiments, the procedure may further comprise, after step b), removing the first and second tubes from the inner lumen of the component by proximally moving them with respect to the component through the proximal opening and/or the first and second, respectively, proximal sub-openings of the component along the guide wire towards the first and second, respectively, free end portions of the guide wire.

It is noted that all embodiments of the invention disclosed herein may be combined with each other unless it is explicitly stated otherwise. Further, features described with reference to a device/implant/system are intended to be applicable correspondingly as features/steps of procedures/methods described herein and vice versa.

SHORT DESCRIPTION OF THE DRAWINGS

In the drawings, like reference characters, generally refer to similar or the same parts throughout the different views. The drawings are not necessarily to scale, emphasis is instead generally placed upon illustrating the principles of the invention.

DETAILED DESCRIPTION

With reference to the FIGS. 1a, 1b, 1c and 2 an implant 10 for implantation around a circumferential tissue structure 1000 in a heart is provided.

Figure 2:
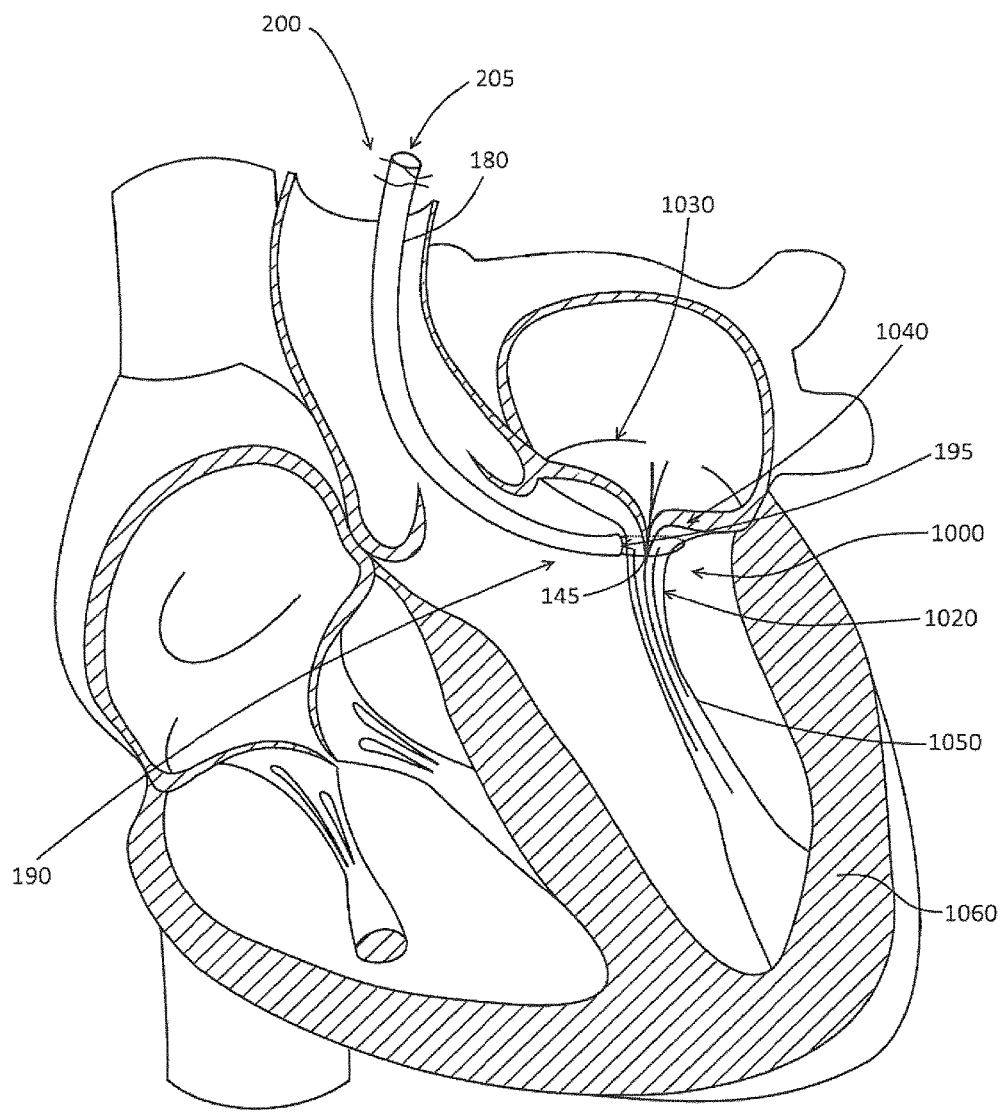
FIG. 2 shows a guide wire surrounding a tissue structure and an outer catheter according to an embodiment of the invention.

The tissue structure 1000 may be a part of a heart, e.g. part of a heart valve such as a aortic valve, mitral valve, pulmonal valve and/or triscupid valve. With reference to FIG. 2, the tissue structure 1000 may e.g. comprise a part of or may be a heart valve (in FIG. 2, a mitral valve is shown) having a connection channel 1020 comprising a connection channel wall structure forming said connection channel 1020 or "through opening". The heart valve may comprise a circumferential valve annulus 1030, valve leaflets 1040 opening and closing the connection channel 1020 at a position close to the valve annulus 1030 to provide a valve-functionality, a generally circumferential chord structure (chordae tendineae) 1050 connecting the valve leaflets 1040 and generally papillary muscle(s) 1060, and said papillary muscles 1060. The circumferential tissue structure 1000 may be said connection channel wall structure 1020. However, the tissue structure 1000 is not limited to the above described tissue structures and may be any circumferential tissue structure 1000 in a human or animal body, such as a blood vessel or the like.

The implant 10 may comprise an elongated component 20. The elongated component 20 may be flexible and/or elastic. The elongated component 20 may include areas with a predetermined rigidity/strength and/or with a predetermined shape at rest, i.e. when there are no external forces applied to the elongated component 20. The elongated component 20 may include one or several hinges. Such (a) hinge(s) may be configured to allow pivoting of portions of the component relative to each other, e.g. in order to facilitate to form a loop with the elongated component 20. The elongated component 20 may include one or several radio-opaque markers for adequate visualization under fluoroscopy. The elongated component 20 may be e.g. made from a plastic material such as PVC, PP, PS, PET, PU, PCU or the like, or may be made from a metal such as a steel alloy, nickel alloy or other metal alloy. The elongated component 20 may e.g. consist of any of the mentioned materials. The elongated component 20 may be configured to be biodegradable. The elongated component 20 may be made from a shape memory alloy such as Nitinol or consist thereof. The elongated component 20 may extend along a longitudinal axis 25 which may be an axis extending through center points of radial cross-sections of the elongated component 20. The elongated component 20 may comprise a first distal end portion 30, a second distal end portion 35 and an intermediate portion 40 which extends between the first 30 and the second 35 distal end portions. The elongate component 20 may comprise a first distal end in the first distal end portion 30 and a second distal end in the second distal end portion 35, which distal ends may define the maximum longitudinal extension of the elongate component 20 and are located in the first 30 and second 35, respectively, distal end portions. That is, the overall length of the component may be defined by the longitudinal distance between the first distal end and the second distal end.

The elongated component 20 may have an outer surface 21 which in a radial cross-section, i.e. a cross-section which is perpendicular to the longitudinal axis 25, has an at least substantially circular or oval shape. However, the outer surface 21 of the elongated component 20 may also have any other shape.

The elongated component 20 may comprise at least one inner lumen 50 which extends longitudinally between the first and second end portions 30, 35 and through the intermediate portion 40. The inner lumen 50 may form a hollow space which extends from the first distal end portion 30 to the second distal end portion 35 along the longitudinal axis 25 and is connected to an outside of the elongated component via a first distal opening 80, which is provided on the first distal end portion 30, and a second distal opening 90, which is provided on the second distal end portion 35. The inner lumen 50 may have an "outer" surface (e.g. an "inner" surface of the component 20) which has an at least substantially circular or oval shape in a radial cross-section of the elongated component 20. However the outer surface of the inner lumen 50 may have any other shape. While the elongated component 20 is shown and described mainly with one inner lumen 50, the elongated component 20 may comprise more than one inner lumen, for example two, three, four, five or more inner lumens.

The elongated component 20 is further provided with at least one proximal opening 100 which is provided on the intermediate portion 40 and connects the inner lumen 50 with the outside of the elongated component 20. The proximal opening 100 may have a distance along the longitudinal axis 25 from the first distal end portion 30 and from the second distal end portion 35. That is, the proximal opening 100 may be located longitudinally between the first distal end portion 30 and the second distal end portion 35 on the elongated component 20. The longitudinal distance between the first distal end portion 30 (e.g. the first distal opening 80) and the proximal opening 100 and the distance between the second distal end portion 35 (e.g. the second distal opening 90) and the proximal opening 100 may be at least substantially equal, e.g. equal. For example, the difference between both distances may be smaller than e.g. 20%, 10% or 5% of the overall longitudinal length from the first 80 to the second 90 distal opening. However, the distances between the proximal opening 100 and the first and second, respectively, distal end portions 30, 35 (and/or the first and second distal opening 80, 90) may also be at least substantially uneven/different, e.g. may one distance have a length corresponding to maximally 10%, 20%, 30%, 40%, 50%, 60%, 70%, 80% or 90% of the length of the other distance. A difference between said distances may e.g. allow to place the implant 10, e.g. a locking means 60 thereof (further described below), at a predefined position with respect to the anatomy. This may be beneficial, as the tissue structure 1000 may not be symmetrical (e.g. when the tissue structure 1000 is part of a mitral valve) and therefore, a predefined position of the implant 10, e.g. of the locking means 60 thereof, which may have a non-uniform outer diameter (with respect to and along longitudinal axis 25), with respect to the tissue structure 1000 may further increase efficiency and/or fixation strength of the implant 10. Any distance or position described herein which refers to a distal end portion 30, 35 as a reference may use the corresponding distal end of the component 20 and/or the corresponding distal opening 80, 90 as a reference. Any distance or position described herein which refers to an opening as a reference may refer to a center of said opening as a reference.

The proximal opening 100 may comprise sub openings, for example a first sub opening 101 and second sub opening 102, which are separate from each other and both connect the inner lumen 50 with the outside of the elongated component 20. The first and second proximal sub openings 101, 102 may be located adjacent to each other. In this respect, the longitudinal distance, that is the distance along longitudinal axis 25, between the first proximal sub opening 101 and the second proximal sub opening 102 may be at least 10 times smaller, e.g. at least 15, 20, 25 or 30 times smaller, than the distance between the first distal opening 80 and the first proximal sub opening 101 and/or the distance between the second distal opening 90 and the second proximal sub opening 102. As described herein, a dimension that is "x times smaller than a second dimension" may have a value corresponding to 1/x of said second dimension.

For example, the longitudinal distance between the first distal end portion 30 (e.g. the first distal opening 80) and the first proximal sub opening 101 may be at least substantially equal to, e.g. equal to, the longitudinal distance between the second distal end portion 35 (e.g. the second distal opening 90) and the second proximal sub opening 102. For example, the difference between said above-mentioned distances may be smaller than e.g. 20%, 10% or 5% of the overall longitudinal length from the first 80 to the second 90 distal opening. However, the distances between the first proximal sub opening 101 and the first distal end portion 30 (and/or the first distal opening 80) and between the second proximal sub opening 102 and the second distal end portion 35 (and/or the second distal opening 90) may also be at least substantially uneven/different, e.g. may one distance have a length corresponding to maximally 10%, 20%, 30%, 40%, 50%, 60%, 70%, 80% or 90% of the length of the other distance. As described above, a difference between said distances may e.g. allow placing the implant 10 (e.g. the locking means 60 thereof) at a predefined position with respect to the tissue structure 1000. The overall length of the component 20 may for example be the sum of the longitudinal distance between the first distal opening 80 and the first sub opening 101, longitudinal distance between the first sub opening 101 and the second sub opening 102, and the longitudinal distance between the second sub opening 102 and the second distal opening 90, when the first and second distal openings 80, 90 are axial end openings of the component 20 and when the proximal opening 100 is formed by first and second sub openings 101, 102. The longitudinal positions of the first distal opening 80 and the the second distal opening 90 may be symmetric or may be asymmetric with respect to the longitudinal axis 25 of the component with the longitudinal position of the proximal opening 100 as a center, wherein, when the proximal opening 100 comprises first and second sub openings 101, 102, said center may be defined longitudinally half-way between the first sub opening 101 and the second sub opening 102.

The first distal opening 80 may be a distal end opening provided in a distal frontal end of the first distal end portion 30. That is, the first distal opening 80 may be an axial opening of the elongated component 20. The first distal opening 80 may however also be spaced from the first distal end of the elongated component 20.

The second distal opening 90 may be a distal end opening provided in a distal frontal end of the second distal end portion 35. That is, the second distal opening 90 may be an axial opening located opposite the first distal opening 80 of the elongated component 20. The second distal opening and 90 may however also be spaced from the second distal end of the elongated component 20.

The first distal opening 80 may have a smaller diameter than the second distal opening 90. For example, the first distal opening 80 may have a diameter that at least substantially equals a diameter of the guide wire 130 (described below), whereas the second distal opening 90 may have a diameter that allows to insert the first distal end portion 30 into the second distal opening 90 as will be described further below. The proximal opening 100 may have a diameter that is at least twice the diameter of the guide wire 130. The first and/or second proximal sub openings 101, 102 may each have a diameter that at least substantially equals the diameter of the guide wire 130, or may each have a larger diameter.

The first distal opening 80, the second distal opening 90, the proximal opening 100 (or the first or second proximal openings 101 and 102 thereof) may be configured so as to enable a sliding motion of the guide wire 130 and to avoid any damage to the guide, wire 130, e.g. when there is relative movement between the elongated component 20 and the guide wire 130. For example, the component 20 may have specific tolerances or a coating to facilitate a relative movement/motion between the guide wire 130 and the component 20. Any or all opening(s) described herein may comprise a smooth surface and/or rounded edges to facilitate movement of the component 20 with respect to the guide wire 130.

The outer surface 21 of the component 20 may have different outer diameters. For example, the second distal end portion 35 may have a larger outer diameter than the intermediate portion 40 and/or the second distal end portion 35. In this respect, the implant 10 may have a maximum outer diameter in a portion corresponding to the second distal end portion 35 of the component 20 (c.f. FIG. 4), at least when the implant 10 forms a (closed) loop.

The implant 10 may further comprise locking means 60 for allowing the first distal end portion 30 to be fixedly connected to the second distal end portion 35. When the first distal end portion 30 is fixedly connected to the second distal end portion 35, the elongated component 20 may form a closed loop as it is shown exemplarily in FIG. 1*c*. Said locking means 60 may be releasable, that is, the first distal end portion 30 and the second distal end portion 35 may be selectively separated from each other after being fixedly connected to each other. Said locking means may alternatively be not-releasable, that is, the first distal end portion 30 may not be disconnected/separated from the second distal end portion 35 without (e.g. irreversibly) changing (e.g. breaking or destroying) implant 10, once said first and second distal end portions 30, 35 are fixedly connected with each other. Such a configuration of the locking means 60 may e.g. be used if the implant 10 is intended to remain in the body of a patient permanently.

The locking means 60 may for example comprise (e.g. consist of) the first distal end portion 30 and the second distal opening 90 of the component 20. In order to fixedly connect the first distal end portion 30 with the second distal end portion 35, the first distal end portion 30 may be inserted into the second distal opening 90. For example, the first distal end portion 30 may be held in the second distal opening 90 by a form fit and/or by a press fit and/or otherwise.

In order to increase a locking force of the locking means 60 which fixedly connects the first and second distal end portions 30, 35, the implant 10 may have a larger outer diameter in an portion corresponding to the locking means 60 than in a portion corresponding e.g. to the intermediate portion 40, at least when the implant 10 forms a loop. Such a larger outer diameter may allow larger dimensions of the constituents of the locking means 60 resulting in a higher locking force. As mentioned above, by dimensioning the distances between the first and second distal end portions 30, 35 (and/or the respective first and second distal opening 80, 90 thereof) and the proximal opening 100 (and/or the sub-openings 101, 102 thereof), said portion of the implant 10 having a larger outer diameter may be placed at a predefined position with respect to the tissue structure 1000. Said larger outer diameter larger outer diameter of the implant in a portion thereof corresponding to the locking means may be the maximum outer diameter of the implant 10.

Figure 3A:
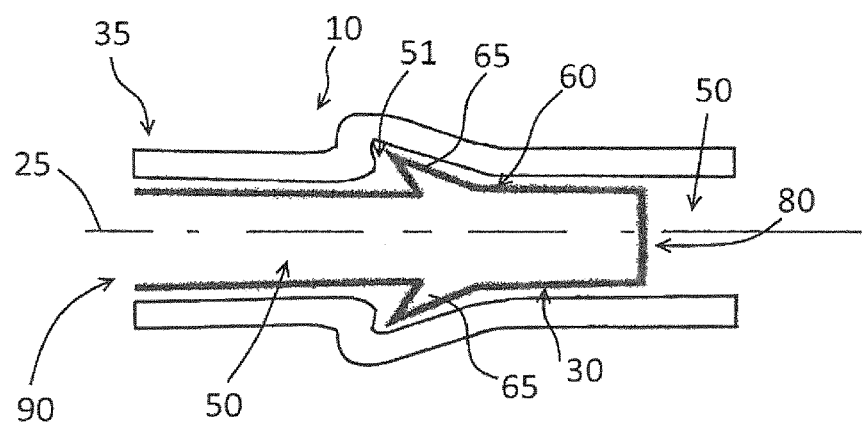
FIG. 3a shows a schematic cross sectional view of a locking means of an implant in a locked state according to an embodiment of the invention.
Figure 3B:
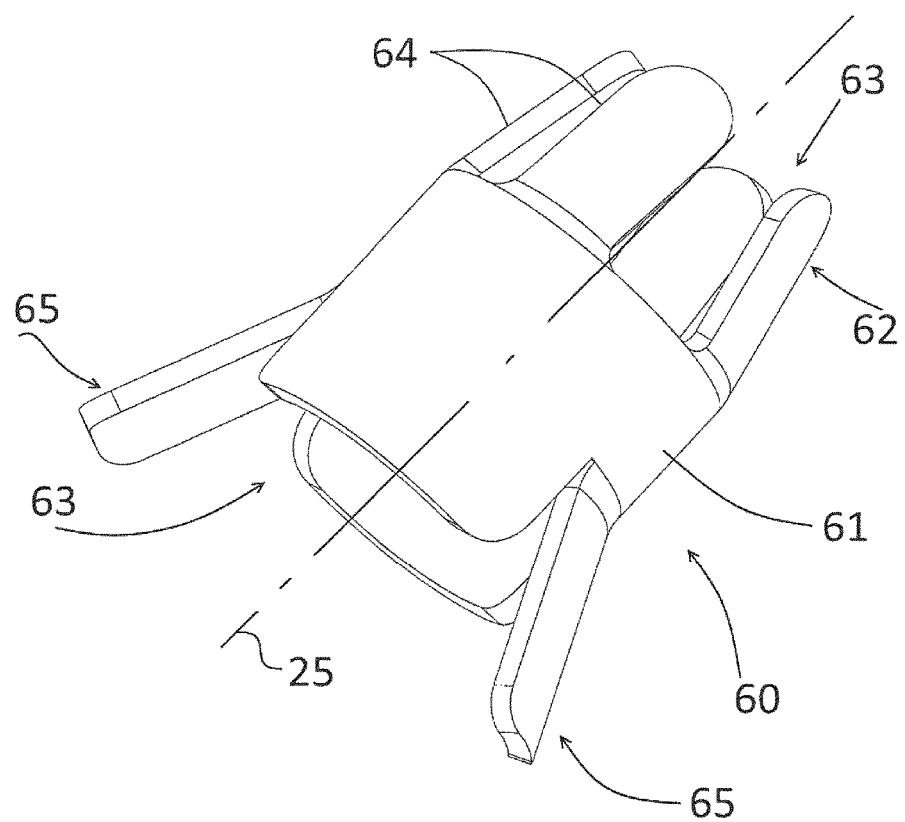
FIG. 3b shows a perspective view of a locking means according to an embodiment of the invention.

With further reference to FIGS. 3*a* and 3*b*, the locking means 60 may optionally for example further comprise at least one protrusion 65, e.g. two, three, four, five or a plurality of protrusions 65. The protrusion(s) 65 may protrude outwards in a radial direction from an outside of the first distal end portion 30. The protrusions 65 may be equi-distantly spaced around a circumference of the first distal end portion 30. The protrusions 65 may be provided at the same axial level of the component 20 or there may be longitudinal distance between the protrusions 65. That is, there may be several, e.g. two, three, four or more, rows of protrusions 65 provided, wherein, when a row comprises more than one protrusion 65, the protrusions 65 in each row may have the same distance from each other around a circumference of the component 20, and wherein the rows may have a longitudinal distance from each other.

The protrusion(s) 65 may optionally additionally protrude backwards with respect to the first distal frontal end of the first distal end portion 30, that is, the protrusion(s) 65 may extend in a direction longitudinally towards the intermediate portion 40 and the second distal end portion 35, as is schematically shown e.g. in FIG. 3a.

In this respect, the protrusion(s) 65 may be formed as an anchor or a barb. Each protrusion 65 may for example have rounded or sharp edges. Each protrusion 65 may for example have a smooth or a rugged surface. Each protrusion 65 may comprise several smaller protrusions or bumps on its surface in order to increase a locking force between the protrusion and the second distal opening 90.

The protrusion(s) 65 may be integrally formed with the first distal end portion 30. For example the protrusion(s) 65 may be monolithically (e.g. monolithically and integrally) formed with the first distal end portion 30. The protrusion(s) 65 may also be provided as a separate component that is fixedly attached to the first distal end portion 30, for example by gluing, welding, sewing, a press fit, and/or a form fit or a combination thereof. The protrusion(s) 65 may e.g. be made from a material which is stronger than the material of the component 20, e.g. the second distal end portion 35 thereof. In this respect, the protrusion(s) 65 may for example be made from a metal/alloy and/or a plastic material as mentioned above, or may consist of such a material. For example, the component 20 may be made from a plastic material and the locking means 60, e.g. the protrusion(s) 65 thereof, may be made from a metal material which may be stronger than the plastic material. However, the locking means 60 may also comprise or consist of the same material as the first and/or the second distal end portion 30, 35.

FIG. 3b shows an example of locking means 60. The locking means 60 comprises an annular body 61 having a reduced diameter section 62 and said protrusions 65 (here two, but the annular body 61 may also be provided with only one protrusion 65 or more than two protrusions 65). The protrusions 65 protrude radially outwards from the annular body 61 and protrude at the same time longitudinally towards the second distal end portion 35.

The annular body 61 defines a through opening 63, and the reduced diameter section 62 protrudes radially inwards into said through opening 63. Here, the reduced diameter section 62 comprises projections (e.g. protrusions) 64 which radially protrude inwards and at the same time axially protrude in a direction opposite to the protrusions 65, i.e. the projections 64 protrude axially "forward" towards the first distal end. When the locking means 60 is fixedly attached on the elongated component 20, the locking means 60 may be provided such that the elongated component 20 extends through the through opening 63, wherein the outer surface 21 of the component 20 is in contact with the projections 64, and the annular body 61 is axially fixed on the elongated component 20 by the reduced diameter section 62, wherein the projections 64 elastically and/or plastically deform the elongate component 20 in order to axially fix the annular body 61 on the elongate component 20, e.g. the first distal end portion 30 thereof. While the annular body 61 that is shown in FIG. 3b comprises the reduced diameter section 62, the annular body 61 may also be fixed in other ways to the elongate component 20, for example by gluing, welding, sewing, a press fit, and/or a form fit or a combination thereof.

As mentioned, to implement the locking means 60, the first distal end portion 30 may be configured so that it can engage into the second distal opening 90. That is, the first distal end portion 30, e.g. with the protrusion(s) 65 provided thereon, may be configured such that it can be inserted into the second distal opening 90. When the first distal end portion 30 is inserted into the second distal opening 90, the locking means 60 may hold the first distal end portion 30 in the second distal opening 90 so that the elongated component 20 forms a closed loop, e.g. around a circumferential tissue structure 1000.

At least the inner portion 51 of the second distal end portion 35, e.g. of the second distal opening 90 thereof, may be provided in a flexible (e.g. elastic) manner, so as to allow the first distal end portion 35 and/or the protrusion(s) 65 to radially expand said inner portion 51 and to be longitudinally anchored in said inner portion 51. Said inner portion 51 of the second distal opening 90 may correspond to the inner lumen 50 of the component 20. For example, when the locking means 60 comprises one or more protrusions 65, the protrusion(s) 65 may elastically deform the second distal end portion 35, e.g. the inner portion 51 of the second distal opening 90, such that protrusion(s) 65, which is/are fixedly attached on the first distal end portion 30, is/are engaged in the second distal opening 90, so as to form a closed loop. The locking means 60 may be configured such that there is no penetration into the elongate component 20, and that the first and second distal end portions 30, 35 are fixedly connected e.g. by elastic forces only. In this respect, the locking means 60 may be configured such that there is at least substantially no permanent/irreversible deformation of the implant 10 or any of its constituents when the first and second distal end portions 30, 35 are fixedly connected with each other.

The axially backwards (i.e. in a direction from the first distal end portion 30 longitudinally along component 20 towards the second distal end portion 35) protruding shape of the protrusion(s) 65 may facilitate inserting the first distal end portion 30 with the locking means 60 into the second distal opening 90 and may also increase the locking force which acts against a force acting to open the closed loop formed by the elongated component 20, when the first distal end portion 30 is fixedly connected to the second distal end portion 35.

Figure 4A:
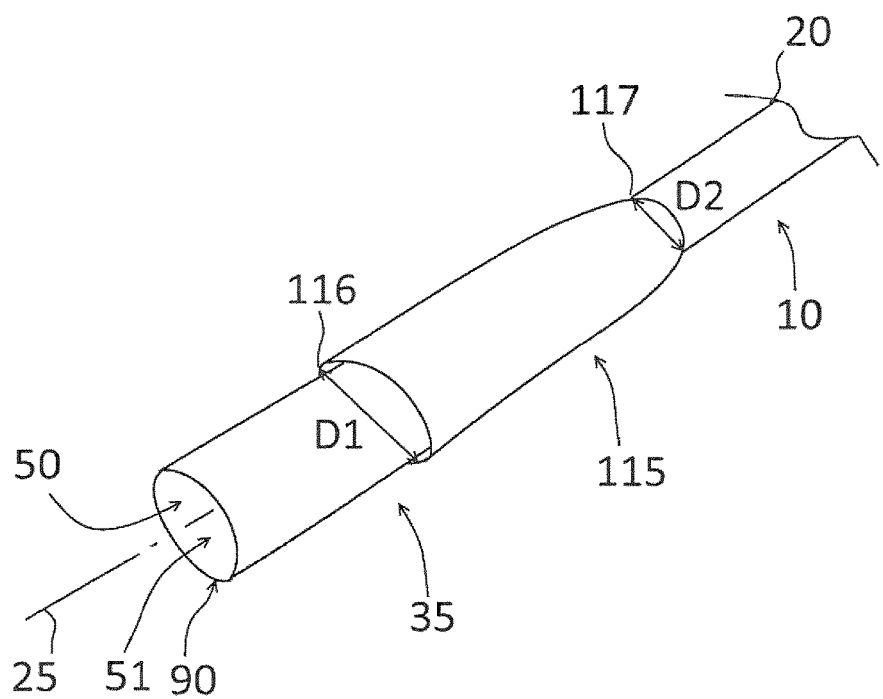
FIG. 4a shows a restricting arrangement according to an embodiment of the invention.
Figure 4B:
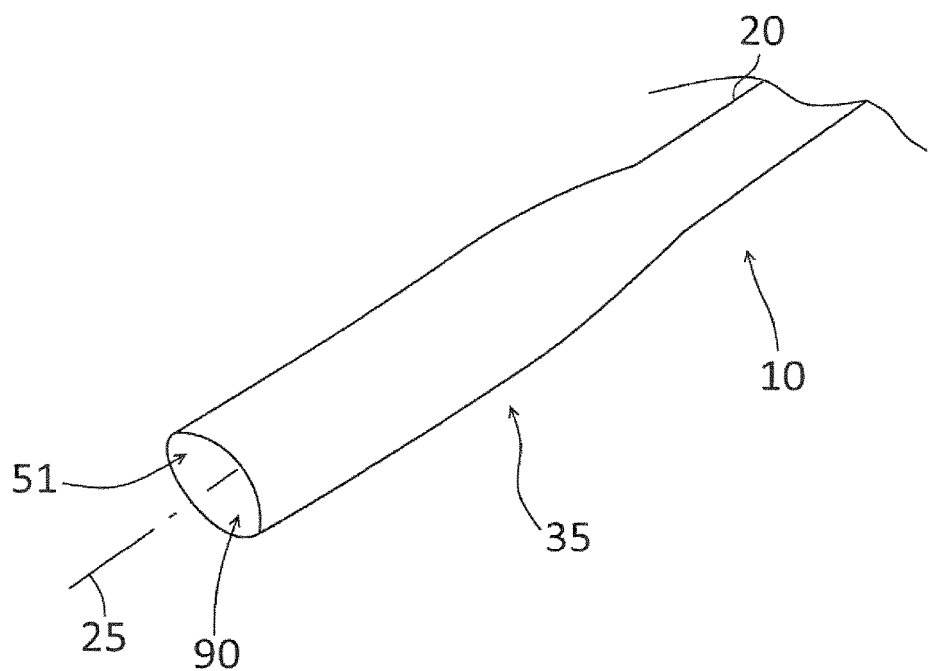
FIG. 4b shows a restricting arrangement according to an embodiment of the invention.

With reference to FIGS. 4a and 4b, the implant 10 may further comprise a restricting arrangement 110 by which a movement, e.g. the longitudinal movement, of the first distal end portion 30 into the second distal opening 90 may be restricted/limited. That is, the restricting arrangement 110 may for example restrict/limit a maximum extension up to which the first distal end portion 30 may be inserted into the second distal opening 90. As shown exemplarily in FIG. 4a, the restricting arrangement 110 may for example comprise an outer sleeve 115 which is provided on an outside of the second distal end portion 35. The outer sleeve 115 may be fixed on the second distal end portion 35. For example, the outer sleeve 115 may be fixed on the second distal end portion 35 by a press fit/interference fit, a form fit, gluing, welding or the like or a combination thereof.

The outer sleeve 115 may have a higher strength, for example a higher radial strength, than the elongate component 20, e.g. the second distal end portion 35 thereof. For example, the outer sleeve 115 may be made from material which is stronger than the material of the second distal end portion 35. The outer sleeve 115 may have different inner diameters. For example, the outer sleeve 115 may define a first inner diameter D1 at a first longitudinal end 116 thereof, which faces the second distal end of the elongate component 20, and may define a second inner diameter D2 at the second longitudinal end 117 thereof, which is longitudinally opposite to the first longitudinal end 116. The first inner diameter D1 may be dimensioned such that the first distal end portion 30 with the locking means 60, which is inserted into the second distal opening 90, may pass through the first inner diameter D1. The second inner diameter D2 may be dimensioned such that the first distal end portion 30 with the locking means 60, which is inserted into the second distal opening 90, may not pass through the second inner diameter D2, so that the movement of the first distal end portion 30 into the second distal opening 90 is restricted by the outer sleeve 115. For example, the inner diameter of the outer sleeve 115 may taper from the first larger inner diameter D1 to the second smaller inner diameter D2 as shown in FIG. 4a.

Alternatively or additionally and as exemplarily shown in FIG. 4b, the restricting arrangement 110 may for example also be realized by a portion of the inner lumen 50 which comprises an inner diameter which (e.g. gradually or abruptly) decreases in the direction away from the second distal opening 90 and into the inner lumen 50 of the elongated component. That is, the inner lumen 50 may be provided such as not to have a constant diameter along the longitudinal axis 25 (e.g. even when there is no outer sleeve 115). Accordingly, a longitudinal movement of the first distal end portion 30 into the second distal opening 90 may be restricted by said decreasing inner diameter. An outer diameter of the elongated component may correspondingly decrease with the decreasing inner diameter of the inner lumen 50, as shown in FIG. 4b. However, the outer diameter of the component 20 may also be constant while the inner diameter of the inner lumen 50 decreases. In this way, for example a restricting arrangement 110 may be realized while maintaining a constant outer diameter of the component 20. The embodiment of the restricting arrangement as shown in FIG. 4b may be realized without any further component such as an outer sleeve 115, however, the outer sleeve 115 may also be provided together with the configuration of the second distal end portion 35 as shown in FIG. 4b.

The restricting arrangement 110 may for example be used to provide a defined diameter of the closed loop which may be formed using the implant 10, as the first distal end portion 30 may be inserted into the second distal opening 90 until further movement thereof is restricted by the restricting arrangement 110 so that the implant 10 forms a closed loop with a defined diameter.

The outer surface 21 of the component 20 may be treated such as to promote tissue ingrowth, e.g. tissue ingrowth of heart tissue. As such, the outer surface 21 of the component 20 may for example be provided with a surface structure (e.g. a specific pattern and/or a specific roughness) and/or with a chemical component, such as pericardium or polyester cloth, which promotes tissue growth. Such ingrowth of tissue may further fixate the implant 10 with respect to the circumferential tissue structure 1000. The implant 10 may also be coated with a drug, e.g. for a controlled delivery of the drug in the circulatory system or in surrounding tissue. The implant 10 may also be coated with a compound that may act as a trap for specific substances in the blood which have an affinity with the compound. The implant 10 (e.g. the component 20 thereof) may also be expandable. The implant 10 (e.g. the component 20 thereof) may be coated with a material swelling over time (e.g. hydrogel). It may also be at least partially inflatable by hydraulic means (e.g. a balloon).

The invention may further provide a system 120 for implanting an implant 10 around a circumferential tissue structure 1000, e.g. in a heart of a patient. Said system 120 may comprise at least one implant 10, e.g. a plurality of implants 10, as described above.

Figure 1A:
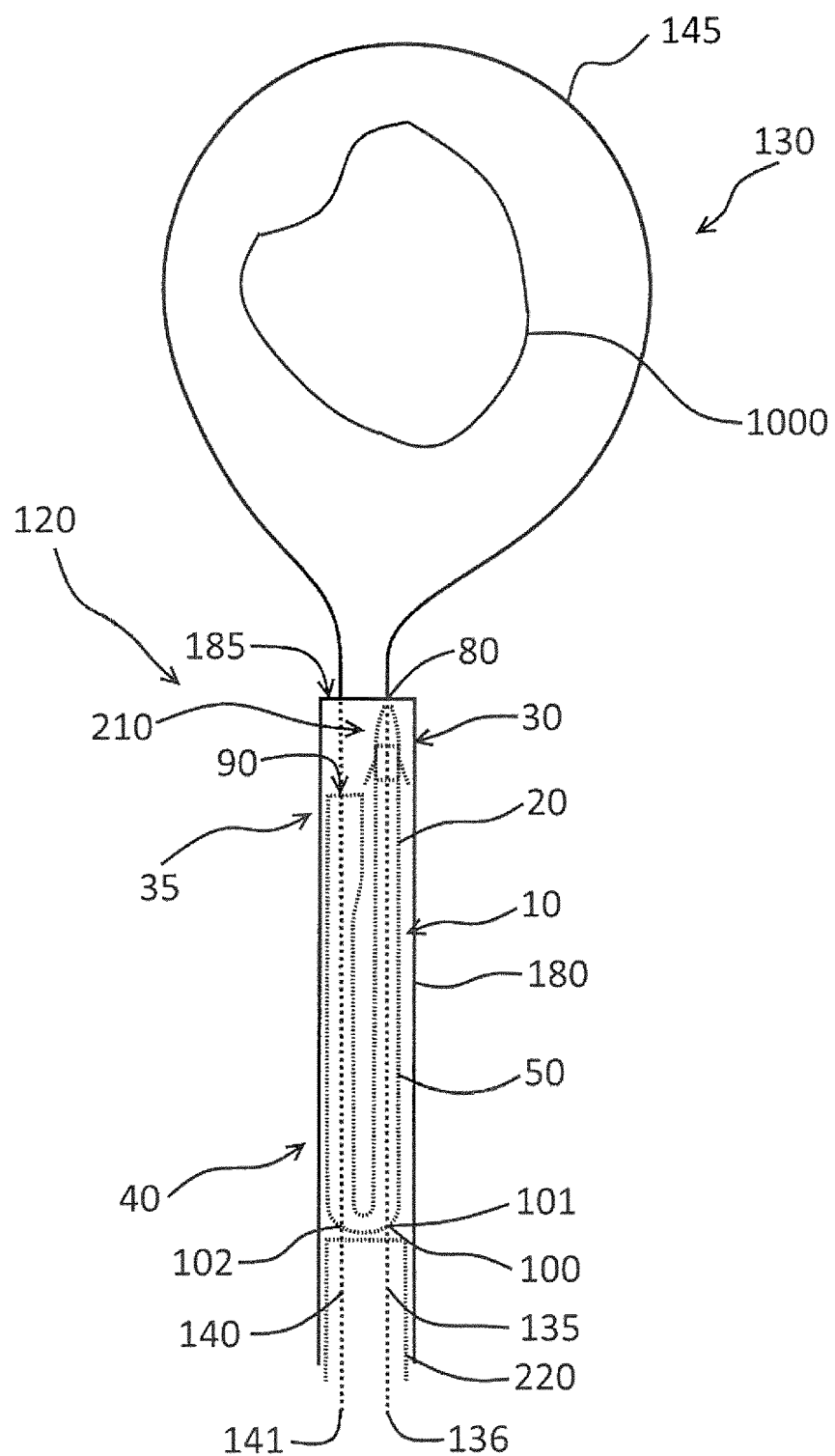
FIG. 1a shows a system for implanting an implant around a circumferential tissue structure in a heart according to an embodiment of the invention.
Figure 1B:
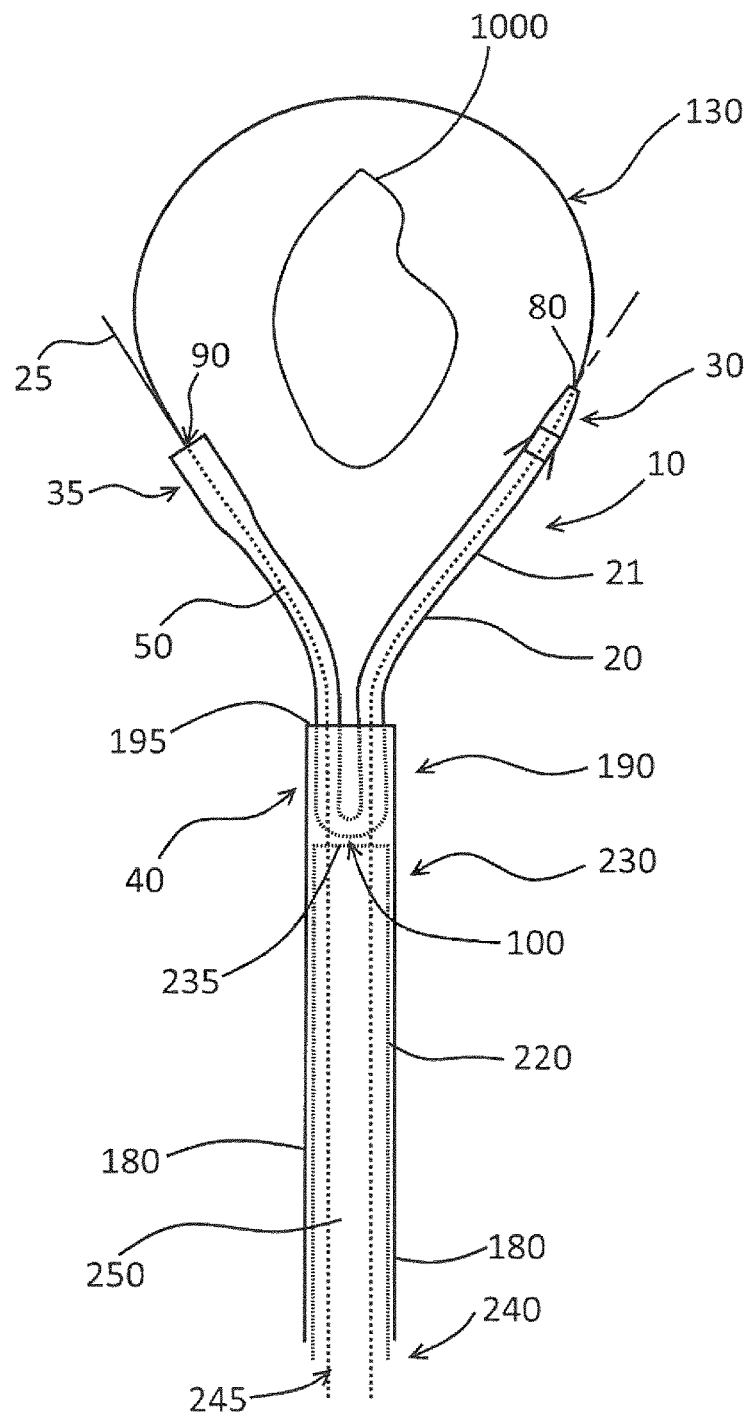
FIG. 1b shows a system for implanting an implant around a circumferential tissue structure in a heart according to an embodiment of the invention.
Figure 1C:
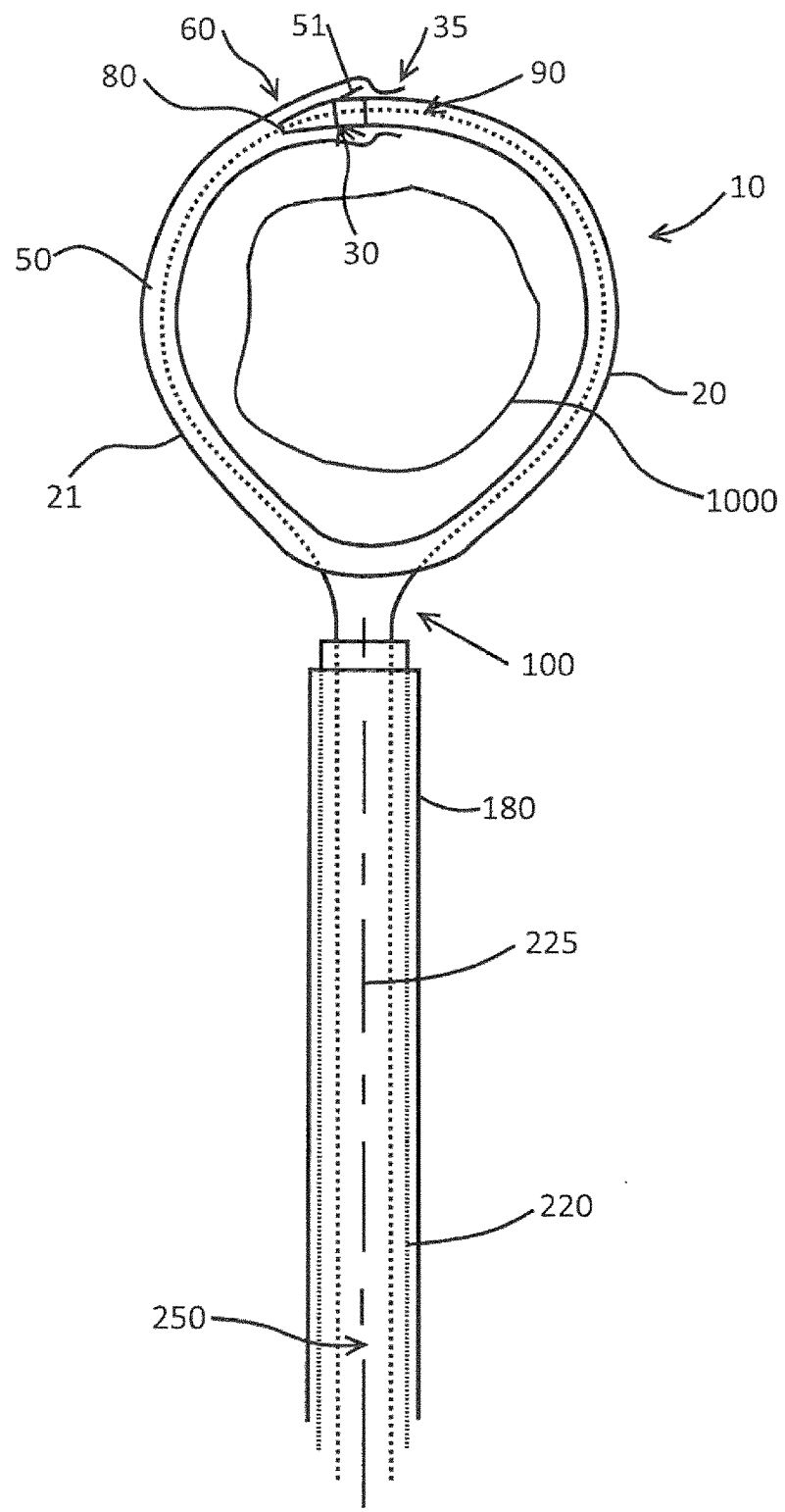
FIG. 1c shows a system for implanting an implant around a circumferential tissue structure in a heart according to an embodiment of the invention, wherein first and second distal end portions of the implant are fixedly connected with each other so as to provide a closed loop.

With reference to FIGS. 1a, 1b and 1c, the system 120 may further comprise a guide wire 130. The guide wire 130 may be flexible, elongate and continuous. The system 120 may for example comprise only one continuous guide wire 130. The guide wire 130 may e.g. be made from metal or plastic material or may e.g. consist of such a material. For example, the guide wire 130 may be made from steel, a shape memory alloy such as Nitinol, PET, PP, PS or nylon or Kevlar or the like, or may consist of any of the mentioned materials.

The guide wire 130 may be configured for surrounding the tissue structure 1000 and may comprise a first leg portion 135 with a first free end portion 136, a second leg portion 140 with a second free end portion 141, and a loop portion 145 which extends between the first 135 and second 140 leg portions and connects said leg portions 135, 140. The guide wire 130 may have such a length that the first and second free end portion 136, 141 are accessible by a surgeon, when the guide wire 130 surrounds the tissue structure 1000. For example, the guide wire 130 may have such a length that the first and second free end portions 136, 141 may be disposed outside the patient's body when the guide wire 130 surrounds the tissue structure 1000.

The guide wire 130 may be disposable or may be disposed in the inner lumen 50 of the component 20 of the implant 10. For example, the guide wire 130 may be disposed such that the first leg portion 135 extends from the first distal opening 80 through the inner lumen 50 to the proximal opening 100 (e.g. the first sub-opening 101), the second leg portion 140 extends from the second distal opening 90 through the inner lumen 50 to the proximal opening 100 (e.g. the second sub-opening 102) and the loop portion 145 extends between the first and second distal end portions 30, 35 as is shown e.g. in FIG. 1b. The first and second free end portions 136, 141 may be proximally exposed from the component.

When the guide wire 130 is disposed in the inner lumen 50 of the component 20, the implant 10 may be movable along the guide wire 130 at least in a distal direction (e.g. towards the tissue structure 1000), wherein the first and second distal end portions 30, 35 are simultaneously movable in a distally leading manner on the first and second leg portions 135, 140 towards and onto the loop portion 145. The intermediate portion 40 may be movable with the component 20 in a proximally trailing manner as is e.g. shown in FIGS. 1b and 1c. That is, the first and second distal end portions 30, 35 may both be located distally with respect to the intermediate portion 40, when the implant 10 is forwarded towards the tissue structure 100.

When the implant 10 is disposed on the guide wire 130 as described above, the first and second distal end portions 30, 35 may come into contact with each other, when the implant 10 is forwarded onto the loop portion 145 (c.f. e.g. FIG. 1c), as the guide wire 130 and the configuration of the implant 10 achieve that the first and second distal end portions 30, 35 may come into contact with each other. In this state, the first and second distal end portions 30, 35 may be fixedly connected to each other using the locking means 60, so that the implant 10 forms a closed loop around the circumferential tissue structure 1000.

For example, forwarding the implant 10 onto the loop portion 145 may cause the first distal end portion 30 and the second distal opening 90 to come into contact with each other, and the first distal end portion 30 and the second distal end portion 35 comprising the second distal opening 90 may be fixedly connected with each other in this state so as to form a closed loop. When the locking means 60 comprises a radial protrusion 65, the radial protrusion 65 which may be provided on the first distal end portion 30, may be forwarded into the second distal opening 90 by forwarding the implant onto the loop portion 145 of the guide wire 130, and may be prevented from exiting the second distal opening 90 by an elastic deformation of at least the inner portion 51 of the second distal opening 90, e.g. by an elastic deformation of the second distal end portion 35.

The system 120 may further comprise an outer catheter 180. The outer catheter 180 may comprise a distal outer catheter end portion 190 having a distal outer catheter opening 195. The outer catheter 180 may comprise a proximal outer catheter end portion 200 having a proximal outer catheter opening 205. An inner lumen 210 of the outer catheter 180 may be connected to the outside of the outer catheter 180 via the distal and proximal outer catheter openings 195, 205. For using the system 120, the outer catheter 180 may be positioned such that the distal outer catheter end portion 190 is placed in the vicinity of the tissue structure 1000 as shown e.g. in FIG. 2. The proximal outer catheter end portion 200 may be positioned such that it is accessible via a surgeon, for example outside of a patient's body. The guide wire 130 may be disposed in the inner lumen 210 of the outer catheter 180 such that the first and second leg portions 135, 140 extend through the inner lumen 210 and the first and second free end portions 136, 141 are exposed from the proximal outer catheter end portion 200 via the proximal outer catheter opening 205. The guide wire 130 may extend from the distal outer catheter opening 195 such that the loop portion 145 is located distally from the distal outer catheter opening 195 and surrounds the tissue structure 1000. The outer catheter 180 is an optional component of the system 120 and may e.g. be used for placing the guide wire 130 around the tissue structure 1000 and/or to facilitate forwarding the implant 10 to the tissue structure 1000 by forwarding the implant 10 through the inner lumen 210 of the outer catheter 180 as will be further described below.

The system 120 may further comprise a pusher catheter 220. The pusher catheter 220 may be at least substantially longitudinal and may extend along a longitudinal axis 225. The pusher catheter 220 may comprise a distal pusher catheter end portion 230 and a proximal pusher catheter end portion 240. The distal pusher catheter end portion 230 may comprise a distal pusher catheter opening 235 connecting an inner lumen 250 of the pusher catheter 220 with an outside of the pusher catheter 220. The proximal pusher catheter end portion 240 may comprise a proximal pusher catheter opening 245 connecting the inner lumen 250 of the pusher catheter 220 with the outside of the pusher catheter 220. The inner lumen 250 may extend from the proximal end portion opening 245 to the distal end portion opening 235 along the longitudinal axis 225 of the pusher catheter 220. The pusher catheter 220 may be used to at least distally move the implant 10 towards and around the tissue structure 1000.

The pusher catheter 220 may be disposed on the guide wire 130 proximally from the implant 10. For example, the pusher catheter 220 may be disposed such that the first and second leg portions 135, 140 of the guide wire 130 extend from the distal pusher catheter opening 235 through the inner lumen 250 to the proximal pusher catheter end opening 245, and the distal pusher catheter end portion 230 either is or can come into contact with the implant 10, e.g. the intermediate portion 40 thereof. The distal pusher catheter opening 235 may be configured such that the implant 10 cannot pass therethrough. Accordingly, the implant 10 may be forwarded towards and around the tissue structure 1000 by distally moving the pusher catheter 220, as the pusher catheter 220 pushes the implant 10 along the guide wire 130 towards and around the tissue structure 1000. Both the pusher catheter 220 and the implant 10 may be forwardable through the inner lumen 210 of the outer catheter 180 and at least the implant 10 may be forwardable from the inner lumen 210 of the outer catheter 180 via the distal outer catheter opening 195.

The pusher catheter 220 may optionally comprise holding means which allows to selectively attach and detach the implant 10 on the distal pusher catheter end portion 230. Accordingly, the implant 10 may not only be moved distally towards and around the tissue structure 1000, but may also be moved proximally along the guide wire 130, e.g. towards the outside of the patient. The holding means may for example be implemented by a controllable hook, a cord, a magnet or the like on the distal pusher catheter end portion 230.

The pusher catheter 220 may be provided with a pusher head 260 on the distal pusher catheter opening 235. The pusher head 260 may be provided with at least one through opening 270 which is sized so as to allow the first and second leg portions 135, 140 of the guide wire 130 to pass through the through opening 270 and to prevent that the implant 10, for example the component 20 thereof, passes therethrough. In this respect, the pusher head 260 may facilitate forwarding the implant 10 by serving as a platform which facilitates pushing the implant 10, as a contact area between the implant and the pusher head 260 may be further increased. The pusher head 260 may be rotatable with respect to the distal pusher catheter end portion 230, e.g around the longitudinal axis 225 thereof, or may be fixed with respect to the pusher catheter 220. A rotatable configuration of the pusher head 260 may for example be advantageous when the leg portions 135, 140 of the guide wire 130 are not extending straight or are entangled with each other, as the pusher head 260 may follow the guide wire 130 more easily and/or may facilitate untangeling the leg portions 135, 140 by rotating relatively to the distal pusher catheter end portion 230. Further, a rotatable pusher head 260 may prevent the formation of twists/entanglements of the first and second leg portions 135, 140 longitudinally between the pusher head 260 and the implant 10 when the implant 10 is forwarded towards or around the tissue structure 1000.

Figure 5A:
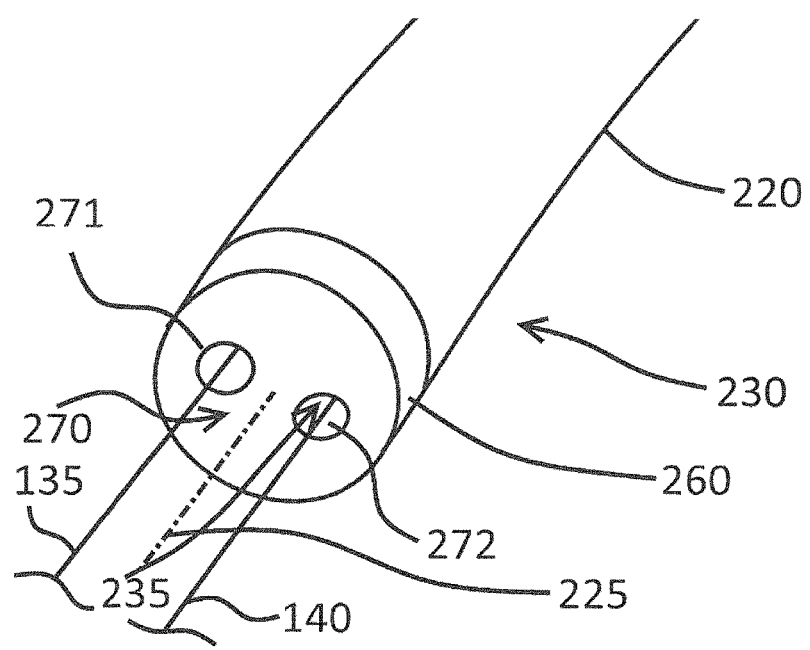
FIG. 5a shows a pusher catheter according to an embodiment of the invention.

FIG. 5*a* shows an exemplary embodiment of the pusher head 260, wherein the pusher head 260 comprises a through opening 270 having a first 271 and a second 272 sub-through opening which are sized so as to allow the first and second leg portions 135, 140, respectively, of the guide wire 130 (and e.g. first and second tubes 160, 170) to pass therethrough and to prevent that the implant 10 can pass therethrough.

Figure 5B:
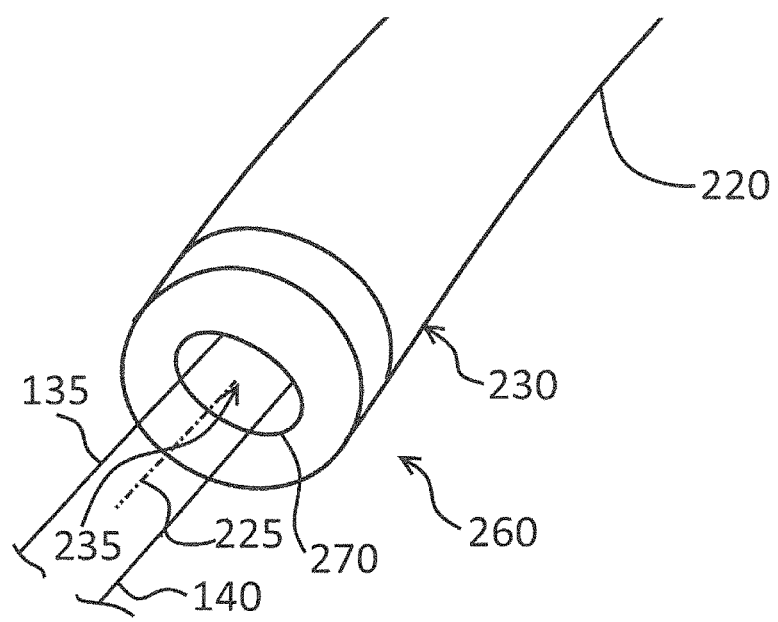
FIG. 5b shows a pusher catheter according to an embodiment of the invention.

FIG. 5*b* shows a further exemplary embodiment of a pusher head 260 which is provided with a through opening 270. As described above, the through opening 270 is dimensioned such that both the first and the second leg portion 135, 140 of the guide wire 130 may pass therethrough. However, at the same time, the through opening 270 is dimensioned such that the implant 10, at least when it is disposed on the guide wire 130, cannot pass therethrough. Accordingly, the pusher head 260 may facilitate moving the implant 10 with respect to the guide wire 130 by providing a further increased contact area between the implant 10 and the pusher catheter 220. While the shown through opening 270 has an oval cross-section, the through opening 270, the first 271 and/or second 271 sub-through openings may e.g. also have a circular, rectangular, square, triangular or other shape.

Figure 5C:
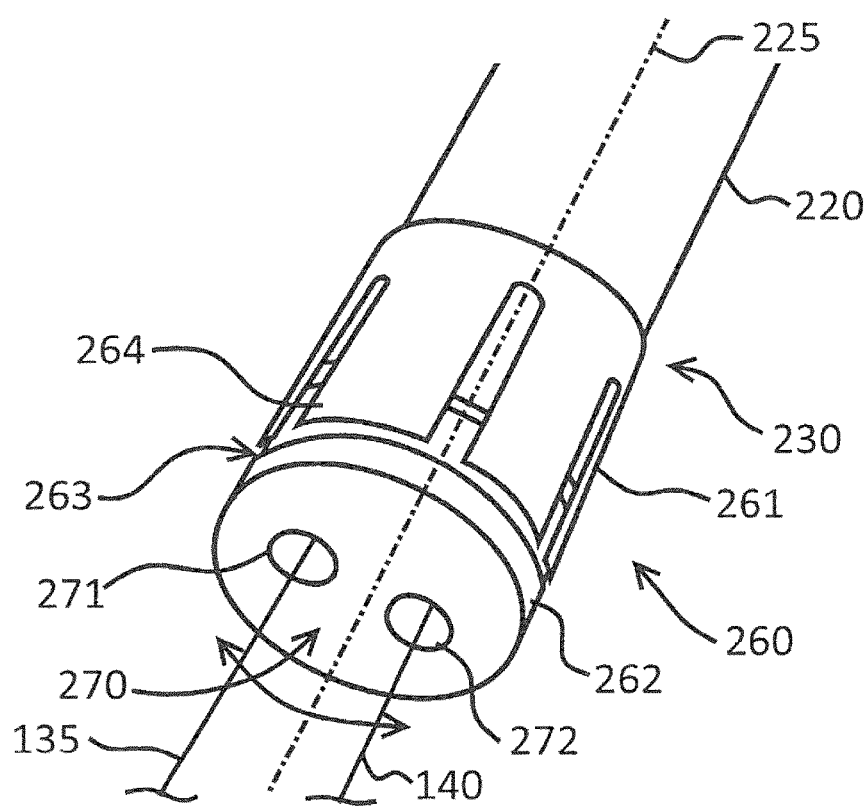
FIG. 5c shows a pusher catheter according to an embodiment of the invention.

FIG. 5*c* shows a further exemplary embodiment of pusher head 260. The pusher head comprises first and second sub-through openings 271 and 272 and is rotatable around longitudinal axis 225 of the pusher catheter 220 with respect to the distal pusher catheter end portion 230. As is shown in FIG. 5c, in one embodiment, the pusher head may 260 comprise a static part 261 which is fixedly attached to the distal pusher catheter end portion 230 and a rotatable part 262 which comprises first and second sub through openings 271, 272 and is rotatable with respect to the static part 261. The rotatable part 262 may for example be connected with the static part 261 by a bearing, e.g. a ball bearing, a slide bearing or the like. The rotatable part 262 may, as is shown in FIG. 5c, also comprise a circumferential groove 263, and the static part 261 may comprise protrusions 264 which engage in the circumferential groove 263, so that the rotatable part 262 is axially fixed with respect to the static part 261 but is rotatable around longitudinal axis 225.

Figure 6:
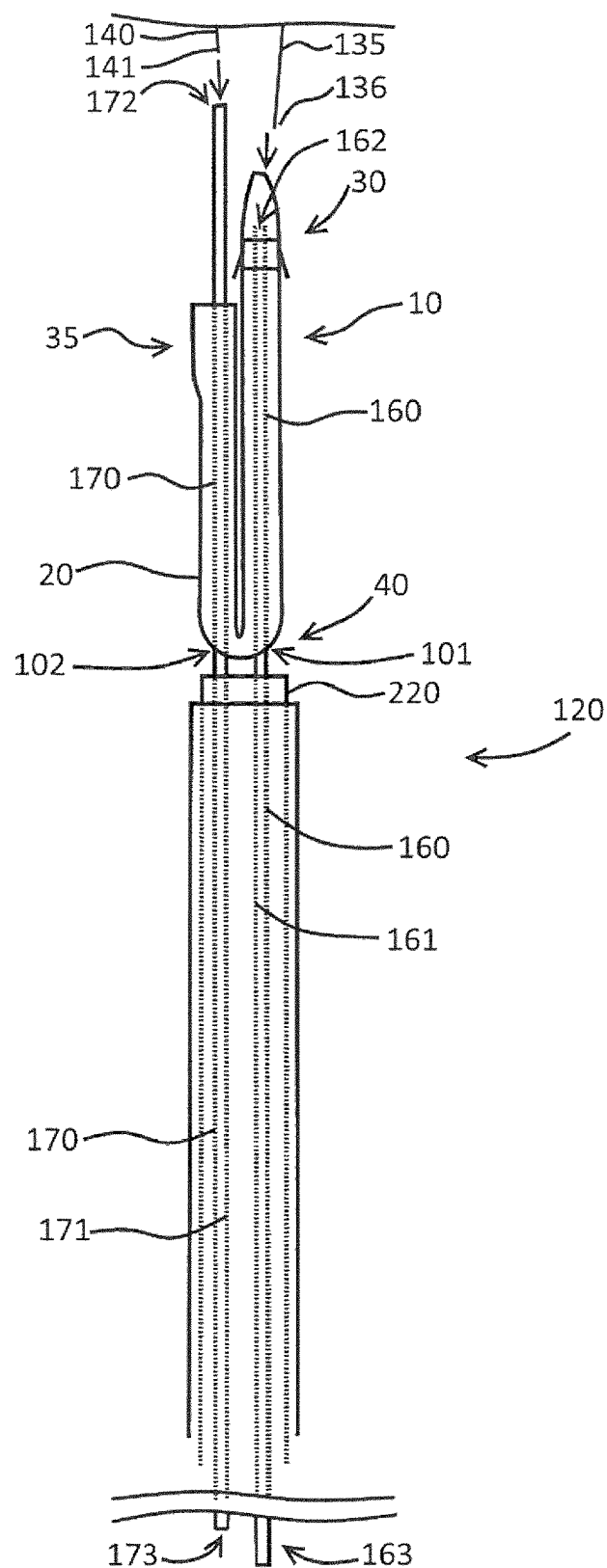
FIG. 6 shows an implant, first and second tubes and a pusher catheter according to an embodiment of the invention.

With further reference to FIG. 6, the system 120 may optionally further comprise a first tube 160 and/or a second tube 170. The first 160 and second 170 tubes may extend at least through a (e.g. longitudinal) portion of the inner lumen 50 of the component 20 and may be removable therefrom. Each tube 160, 170 may have an inner lumen 161, 171 extending longitudinally therethrough from a distal end opening 162, 172 to a proximal end opening 163, 173 of each tube 160, 170.

The first tube 160 may be positioned in the inner lumen 50 of the component 20 such that it extends at least through a portion of the inner lumen 50 and out of the proximal opening 100 (e.g. the first sub-opening 101 of the proximal opening 100). The distal end opening 162 of the first tube 160 may be located longitudinally between the proximal opening 100 (e.g. the first sub-opening 101) and the first distal opening 80 in the inner lumen 50 of the component 20. Optionally, the first tube 160 may extend out of the inner lumen 50 through the first distal opening 80 of the component 20, e.g. such that the distal end opening 162 is exposed distally therefrom. The proximal end opening 163 of the first tube 160 may be exposed (proximally) from the proximal opening 100 (e.g. the first sub-opening 101)

The second tube 170 may be positioned in the inner lumen 50 of the component 20 such that it extends at least through a portion of the inner lumen 50 of the component 20 and out of the proximal opening 100 (e.g. the second sub-opening 102 of the proximal opening 100). The distal end opening 172 of the second tube 160 may be located longitudinally between the proximal opening 100 (e.g. the second sub-opening 101) and the second distal opening 90 in the inner lumen 50 of the component 20. Optionally, the second tube 170 may extend out of the inner lumen 50 through the second distal opening 90 of the component 20, e.g. such that the distal end opening 172 is distally exposed therefrom. The proximal end opening 173 of the second tube 170 may be exposed (proximally) from the proximal opening 100 (e.g. the second sub-opening 102).

When the system 120 comprises a pusher head 260, the first tube 160 may optionally further extend through the through opening 270 (e.g. the first sub-opening 271) of the pusher head 260 so that the proximal end opening 173 of the first tube 170 is located proximally from the pusher head 260 (e.g. proximally from the proximal end opening 245 of the pusher catheter 220). Optionally, the distal end opening 162 of the first tube 160 may be located distally from the first distal opening 80 of the component 20 at the same time. Similarly, when the system 120 comprises a pusher head 260, the second tube 170 may optionally further extend through the through opening 270 (e.g. the second sub-opening 272) of the pusher head 260 so that the proximal end opening 173 of the second tube 170 is located proximally from the pusher head 260 (e.g. proximally from the proximal end opening 245 of the pusher catheter 220). Optionally, the distal end opening 172 of the second tube 170 may be located distally from the second distal opening 90 of the component 20 at the same time.

The first 160 and second 170 tubes may for example facilitate threading the implant 10 onto the guide wire 130. In this respect, the guide wire 130, e.g. the first free end portion 136 thereof, may be inserted into the distal end opening 162 of the first tube 160 and may be moved through the inner lumen 161 of the first tube 160 (e.g. by pushing the first leg portion 135 of the guide wire 130) so that the first free end portion 136 of the guide wire 130 exits the inner lumen 161 of the first tube 160 via the proximal end opening 163 of the first tube 160 and consequently, the first leg portion 135 extends through the first tube 160 which itself extends (at least partially) through the component 20 (and optionally the pusher head 260) as described above.

Further, the guide wire 130, e.g. the second free end portion 141 thereof, may be inserted into the distal end opening 172 of the second tube 170 and may be moved through the inner lumen 171 of the second tube (e.g. by pushing the second leg portion 140 of the guide wire 130) so that the second free end portion 141 of the guide wire 130 exits the inner lumen 171 of the second tube 170 via the proximal end opening 173 of the first tube 170 and consequently, the second leg portion 140 extends through the second tube 170 which itself extends (at least partially) through the component 20 (and optionally the pusher head 260) as described above. When the guide wire 130 extends through the first and second tubes 160, 170 as described above, the first and second tubes 160, 170 may be removed proximally from the inner lumen 50 of the component 20, while the guide wire 130 may be, at least substantially, be held in place relative to the component 20 (and e.g. the pusher head 260). For example, the first and second tubes 160, 170 may be moved proximally over the first and second, respectively, free end portion 136, 141 of the guide wire 130 and may be removed from the system 120.

In this state, the first and second leg portions 135, 140 of the guide wire 130 remain extending through the component 20 (and optionally through the pusher head 260) as described above. Accordingly, the first and second tubes 160 may facilitate threading the guide wire 130 through component 20 (and optionally the pusher head 260), as the first and second free end portions 136, 141 each only have to be threaded through the distal end opening of the respective tube 160, 170 and may be forwarded through the inner lumen of said tube 160, 170.

To schematically show the above-described threading of the guide wire 130 into the first and second tubes 160, 170, the first and second leg portions 135, 140 with their respective free end portions 136, 141 are schematically shown in FIG. 6 distally from the first and second tubes 160, 170 together with an arrow indicating the direction of insertion of the free end portion 136, 141 into the respective first or second tube 160, 170. To schematically show the removal of the first and/or second tube 160, 170 in a proximal direction from the implant 10, the first tube 160 is shown in FIG. 6 partially retracted in a proximal direction.

In this respect, a method for disposing and forwarding an implant 10 on the guide wire 130 of a system 120 may comprise threading the first leg portion 135 of the guide wire 130 with its first free end portion 136 into the first distal opening 80 and out through the proximal opening 100 and/or the first proximal sub-opening 101, threading the second leg portion 140 of the guide wire 130 with its second free end portion 141 into the second distal opening 90 and out through the proximal opening 100 and/or the second proximal sub-opening 102. When the implant 10 comprises the first 160 and/or second tube 170, the afore-mentioned method may further include threading the first leg portion 135 of the guide wire 130 with its first free end portion 136 into the first distal end opening 162 of the first tube 160 and out through the proximal end opening 163 of the first tube 160 and/or threading the second leg portion 140 of the guide wire 130 with its second free end portion 141 into the distal end opening 172 of the second tube 170 and out through the proximal end opening 173 of the second tube 170.

The method may further comprise pushing the component 20 on and along the guide wire 130 towards the loop portion 145 thereof to distally approach the first and second distal end portions 30, 35 from opposite direction so as to meet and connect to each other in the loop portion 145 of the guide wire 130.

Such a method may for example be employed during an implantation procedure as a method for disposing and forwarding an implant on a guide wire of a system as described herein to a patient, when the guide wire 130 extends around the tissue structure 1000 as described above and as exemplarily shown in FIG. 2 (the shown approach through the aorta is only shown as an example for one possible approach). However, such a method may also be employed/ performed without any patient and/or surgery, e.g. using a model or training environment.

Further, a method for providing an implant 10 around a circumferential tissue structure 1000 in a heart of a patient using the system 120 as described herein may be carried out as described in the following.

The guide wire 130 may be forwarded by forwarding the first free end portion 136 of the guide wire 130 from an outside of the patient to the tissue structure 1000, around the tissue structure 1000 and back towards the outside of the patient (e.g. using the outer catheter 180), so that the loop portion 145 of the guide wire 130 extends distally around the tissue structure 1000 and the first leg portion 135 extends proximally from the tissue structure 1000 towards the outside of the patient and the second leg portion 140 extends proximally from the tissue structure 1000 towards the outside of the patient, so that the first 136 and second free end portions 141 of the first and second, respectively, leg portions 135, 140 are accessible, e.g. e for a surgeon.

When the guide wire 130 is forwarded by optionally using the outer catheter 180, the outer catheter 180 may be positioned such that the distal outer catheter opening 195 is placed adjacent to the tissue structure 1000. Then, the first free end portion 136 of the guide wire 130 may be forwarded from the proximal outer catheter opening 205 through the outer catheter lumen 210 and from the distal outer catheter opening 195 to the tissue structure 1000, around the tissue structure 1000 and via the distal outer catheter opening 195, the outer catheter lumen 210 and the proximal outer catheter opening 205 towards the outside of the patient again.

In this respect, to forward the guide wire 130 and/or the implant 10 to the tissue structure 1000 (e.g. by using the outer catheter 180) any known approach may be used, for example an arterial retrograde approach entering the heart cavity through the aorta, an approach thorough a venous access optionally through a puncture through the inter atrial septum (trans-septal approach), a trans-apical approach via a puncture through the apex of the heart, and/or an arterial access (e.g. via the femoral artery through a puncture in the groin).

The method may further comprise threading the first leg portion 135 of the guide wire 130 with its first free end portion 136 into the first distal opening 80 and out through the proximal opening 100 and/or the first proximal sub-opening 101 of the component 20, threading the second leg portion 140 of the guide wire 130 with its second free end portion 141 into the second distal opening 90 and out through the proximal opening 100 and/or the second proximal sub-opening 102 of the component 20 as described above. As mentioned above, when the implant 10 comprises the first 160 and/or second tube 170, the afore-mentioned method may further include threading the first leg portion 135 of the guide wire 130 with its first free end portion 136 into the first distal end opening 162 of the first tube 160 and out through the proximal end opening 163 of the first tube 160 and/or threading the second leg portion 140 of the guide wire 130 with its second free end portion 141 into the distal end opening 172 of the second tube 170 and out through the proximal end opening 173 of the second tube 170.

When the system comprises a pusher catheter 220, the method may further comprise threading the first leg portion 135 of the guide wire 130 with its first free end portion 136 into the distal end portion opening 235 of the pusher catheter 220 (e.g. via the through opening 270, e.g. the first sub opening 271 thereof, of the pusher head 260), through the lumen 250 of the pusher catheter 220 and out from the proximal end opening 245 of the pusher catheter 220, and threading the second leg portion 140 of the guide wire 130 with its second free end portion 141 into the distal end portion opening 235 of the pusher catheter 220 (e.g. via the through opening 270, e.g. the second sub opening 272 thereof, of the pusher head 260), through the lumen 250 of the pusher catheter 220 and out through the proximal end opening 245 of the pusher catheter 220.

When the implant 10 comprises first and second tubes 160, 170 and the implant 10 is threaded on the guide wire 130, the method may further comprise proximally removing the first and second tubes 160, 170 while keeping the implant 10 threaded on the guide wire 130. The first and second tubes 160, 170 may e.g. be removed proximally through the proximal opening 100 (e.g. the first 101 and second 102, respectively, proximal sub-opening thereof) of the component 20. The first and second tubes 160, 170 may e.g. also be removed proximally through the through opening 270 (e.g. the first 271 and second 272, respectively, sub-through opening) of the pusher head 260, e.g. towards an outside of the patient.

The method may further comprise pushing the implant 10 on and along the guide wire 130 towards and onto the loop portion 145 of the guide wire 130 to distally approach the first 30 and second 35 distal end portions of the component 20 simultaneously from opposite directions so as to meet and come into contact with each other in the loop portion 145 of the guide wire 130.

For example, the implant 10 may be forwarded by distally pushing the pusher catheter 220 along the guide wire 130, e.g. through the lumen 210 of the outer catheter 180, towards the tissue structure 1000. As the distal end portion 230, e.g. the pusher head 260, is in contact with the implant 10, the pusher catheter 220 may push the implant 10 thereby towards and around the tissue structure 1000 as is exemplarily shown in FIGS. 1a, 1b and 1c, which show an exemplary sequence of forwarding an implant 10 towards and around a tissue structure 1000 using a system 120 according to the invention, wherein in FIG. 1c the implant 10 is shown with first and second distal end portions 30, 35 being in contact with each other so that the implant 10 forms a (full) loop around the tissue structure 1000.

The method may further comprise fixedly connecting the first 30 and second 35 distal end portions of the component 20. Said first 30 and second 35 distal end portions may for example be fixedly connected to each other using the above described locking means 60. When the first and second distal end portions 30, 35 are fixedly connected with each other, the implant 10 forms a fully closed loop as is shown e.g. in FIG. 1c. Said loop may fit loosely around the tissue structure 1000 (e.g. when a diameter formed, by the loop is larger than a diameter of the tissue structure 1000) or said loop may form a press fit around said tissue structure 1000 (e.g. when a diameter formed by the loop is smaller than a diameter of the tissue structure 1000 in its natural state, i.e. without an external force caused by the implant 10 or the guide wire 130 acting upon it).

The implant 10 and system 120 described herein may for example be used to fixate a prosthesis (e.g. a mitral prosthesis) relative to a native heart valve (e.g. a mitral valve, see e.g. FIG. 2). Such a prosthesis may for example comprise an artificial heart valve and may be located inside the connection channel 1020 (c.f. FIG. 2), e.g. of a mitral or tricuspid valve. Then, the implant 10 may be forwarded to and around said connection channel 1020 to form a loop around the outside of the connection channel 1020 and the prosthesis disposed therein. Said loop may secure the prosthesis in the connection channel 1020 e.g. via a form fit or via a frictional fit. However, the implant 10 may also be used for other purposes like forming an artificial annulus, sealing blood leakage, as a stent device etc. Further, the tissue structure 1000 may also be a tissue structure outside a heart, e.g. a structure in a organ such as a kidney, or a blood vessel or the like. Further, the implant 10 may comprises sensors and/or a microsystem which measures anatomical and physical properties in the anatomy such as temperature, pH or pulsatility. The implant 10 may comprise one or several electric coils that create an electrical current under exposure to an electro-magnetic field. This current may then be used to power any sensor/microsystem in the implant 10 or other devices implanted in the body, such as a leadless pacemaker.

Further, the implant 10 may comprise hooks or barbs or the like on the outer surface 21 of the component 20 for engaging the anatomy and for providing further increased fixation in the anatomy. In this respect, the implant 10 may for example be used as a device for annuloplasty.

It is noted that all embodiments described herein may be combined with each other unless it is specifically described otherwise. Further, all features which are described with respect to methods/processes may also be applied as corresponding device features and vice versa.

The invention claimed is:

1. An implant for implantation around a circumferential tissue structure in a heart, the implant comprising:
   a flexible elongated component which has a longitudinal axis and which has a first distal end portion, a second distal end portion and an intermediate portion extending between the first and second distal end portions, and one inner lumen extending longitudinally between the first and second distal end portions and through the intermediate portion; and
   a locking means configured to allow the first distal end portion to be fixedly connected to the second distal end portion so as to provide the elongated component as a closed loop;
   wherein the first distal end portion is provided with a first distal opening which connects the one inner lumen with an outside of the component;
   wherein the second distal end portion is provided with a second distal opening which connects the inner lumen with the outside of the component;
   wherein the intermediate portion is provided with a proximal opening which connects the one inner lumen with the outside of the component, wherein the proximal opening is longitudinally spaced from both the first and second distal openings; and
   wherein the first distal end portion is configured to engage into the second distal opening, the locking means comprises a protrusion which radially protrudes from an outside of the first distal end portion, and when the first distal end portion is in engagement in the second distal opening, the protrusion radially engages with an inner portion of the second distal end portion so as to fixedly secure the engagement of the first distal end portion in the second distal opening.

2. The implant according to claim 1, wherein each of the first and second distal openings is a distal end opening provided in a distal frontal end of the corresponding first and second distal end portions.

3. The implant according to claim 1, wherein a longitudinal distance between the proximal opening and the first distal opening is at least substantially equal to a longitudinal distance between the proximal opening and the second distal opening.

4. The implant according to claim 1, wherein the proximal opening has first and second proximal sub-openings, both of which connect the one inner lumen with the outside of the component and which are located adjacent to each other.

5. The implant according to claim 4, wherein the longitudinal distance between the first distal opening and the first proximal sub-opening is at least substantially equal to the longitudinal distance between the second distal opening and the second proximal sub-opening.

6. The implant according to claim 1, wherein the protrusion is formed as an anchor or barb.

7. The implant according to claim 1, wherein at least the inner portion of the second distal end portion is provided in a flexible manner so as to allow the protrusion to radially expand the inner portion and to be longitudinally anchored in the inner portion of the second distal end portion.

8. The implant according to claim 7, further comprising a restricting arrangement, by which a longitudinal movement of the first distal end portion into the second distal opening is restricted.

9. The implant according to claim 8, wherein the restricting arrangement comprises an outer sleeve provided on the second distal end portion, wherein the outer sleeve has a radial strength stronger than the radial strength of the second distal end portion.

10. The implant according to claim 1, wherein an outer surface of the component is treated with a tissue ingrowth promoting material.

11. A system for implanting an implant around a circumferential tissue structure in a heart of a patient, the system comprising:
    a flexible elongate continuous guide wire for surrounding the tissue structure, which has a first leg portion with a first free end portion, a second leg portion with a second free end portion, and a loop portion extending between and connecting the first and second leg portions, wherein the loop portion is for distally extending around the tissue structure and the first and second leg portions are for proximally extending from the tissue structure towards an outside of the patient so that the first and second free end portions are accessible for a surgeon, and an implant including:
- a flexible elongated component which has a longitudinal axis and which has a first distal end portion, a second distal end portion and an intermediate portion extending between the first and second distal end portions, and one inner lumen extending longitudinally between the first and second distal end portions and through the intermediate portion; and
- a locking means configured to allow the first distal end portion to be fixedly connected to the second distal end portion so as to provide the elongated component as a closed loop;
- wherein the first distal end portion is provided with a first distal opening which connects the one inner lumen with an outside of the component;
- wherein the second distal end portion is provided with a second distal opening which connects the inner lumen with the outside of the component; and
- wherein the intermediate portion is provided with a proximal opening which connects the one inner lumen with the outside of the component, wherein the proximal opening is longitudinally spaced from both the first and second distal openings;

wherein the guide wire is disposable or is disposed in the one inner lumen of the component in a manner so that the loop portion extends between the first and second distal end portions, the first leg portion extends from the loop portion through the first distal opening and through the proximal opening so that the first free portion is proximally exposed from the component, and the second leg portion extends from the loop portion through the second distal opening and through the proximal opening so that the second free end portion is proximally exposed from the component, and wherein the implant is moveable along the guide wire in a distal direction, with the first and second distal end portions being simultaneously moveable in a distally leading manner on the first and second leg portions onto the loop portion.

12. The system according to claim 11, wherein the proximal opening has first and second proximal sub-openings, both of which connect the one inner lumen with the outside of the component and which are located adjacent to each other.

13. The system according to claim 11, further comprising first and second tubes, wherein the first and second tubes removably extend through the inner lumen of the component, with the first tube extending through the proximal opening and/or the first proximal sub-opening, and with the second tube extending through the proximal opening and/or the second proximal sub-opening, and wherein the first leg portion extends through the first tube and the second leg portion extends through the second tube.

14. The system according to claim 11, further comprising an outer catheter having proximal and distal outer catheter end portions with respective proximal and distal outer catheter openings and an outer catheter lumen, wherein the guide wire, with the implant disposed thereon, is disposable through the outer catheter lumen.

15. The system according to claim 14, further comprising a pusher catheter having distal and proximal pusher catheter end portions with respective distal and proximal pusher catheter openings and a pusher catheter lumen, wherein the pusher catheter is configured so as to be disposable through the outer catheter lumen, and wherein the guide wire is configured so as to be partly disposable through the pusher catheter lumen, and wherein the pusher catheter and the implant are configured such that the implant, disposed on the guide wire which itself is partly disposed in the pusher catheter lumen, can be distally pushed on and along the guide wire through the outer catheter lumen.

16. The system according to claim 15, wherein the pusher catheter is provided with a pusher head provided on the distal pusher catheter opening, the pusher head having a through opening sized so as to allow the first and second leg portions of the guide wire to pass therethrough and to prevent the component to pass therethrough.

17. The system according to claim 16, wherein the through opening comprises first and second sub-through openings which are sized so as to allow the first and second leg portions, respectively, of the guide wire to pass therethrough.

18. The system according to claim 16, wherein the pusher head is rotatable relative to the pusher catheter about a longitudinal axis of the pusher catheter.

19. A method for disposing and forwarding an implant on a guide wire of a system according to claim 11, the method comprising:
- threading the first leg portion of the guide wire with its first free end portion into the first distal opening and out through the proximal opening and/or the first proximal sub-opening, threading the second leg portion of the guide wire with its second free end portion into the second distal opening and out through the proximal opening and/or the second proximal sub-opening, and pushing the component on and along the guide wire towards the loop portion thereof to distally approach the first and second distal end portions from opposite direction so as to meet and connect to each other in the loop portion of the guide wire.

* * * * *